US012315641B2

(12) United States Patent
Bae et al.

(10) Patent No.: US 12,315,641 B2
(45) Date of Patent: May 27, 2025

(54) METHOD AND APPARATUS FOR QUANTITATIVE IMAGING USING ULTRASOUND DATA

(71) Applicant: KOREA ADVANCED INSTITUTE OF SCIENCE AND TECHNOLOGY, Daejeon (KR)

(72) Inventors: Hyeon-Min Bae, Daejeon (KR); Seokhwan Oh, Daejeon (KR); Gibbeum Lee, Daejeon (KR); Myeong Gee Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 457 days.

(21) Appl. No.: 17/115,966

(22) Filed: Dec. 9, 2020

(65) Prior Publication Data

US 2021/0183521 A1 Jun. 17, 2021

(30) Foreign Application Priority Data

Dec. 13, 2019 (KR) .................. 10-2019-0166616
Jul. 21, 2020 (KR) .................. 10-2020-0090261

(51) Int. Cl.
*G16H 50/50* (2018.01)
*A61B 8/00* (2006.01)
(Continued)

(52) U.S. Cl.
CPC ........... *G16H 50/50* (2018.01); *A61B 8/4477* (2013.01); *A61B 8/469* (2013.01); *A61B 8/5246* (2013.01); *G06N 3/08* (2013.01); *A61B 8/15* (2013.01)

(58) Field of Classification Search
None
See application file for complete search history.

(56) References Cited

U.S. PATENT DOCUMENTS

2014/0180099 A1* 6/2014 Rothberg ............ A61B 8/13
600/439
2014/0364734 A1 12/2014 Huang
(Continued)

FOREIGN PATENT DOCUMENTS

JP 2012-239546 12/2012
JP 6457157 1/2019
(Continued)

OTHER PUBLICATIONS

Cheng et al. "Deep Learning Image Reconstruction Method for Limited-Angle Ultrasound Tomography in Prostate Cancer", 2019, Medical Imaging 2019: Ultrasound Imaging and Tomography, Proc. of SPIE, vol. 1095516 (Year: 2019).*
(Continued)

*Primary Examiner* — Colin T. Sakamoto
*Assistant Examiner* — Andrew W Begeman
(74) *Attorney, Agent, or Firm* — LEX IP MEISTER, PLLC

(57) ABSTRACT

The method of operating an image device comprises receiving an input of virtual tissues modeled with an arbitrary shape and a quantitative feature, simulating a TOF change or a signal strength change of ultrasound data having penetrated the virtual tissues modeled with a speed-of-sound distribution or an attenuation coefficient distribution in a first and in a second direction, and creating an image pair representing the TOF change or the signal strength change, creating a speed-of-sound distribution image or an attenuation coefficient distribution image of each of the virtual tissues as a ground truth of an image pair created in the corresponding virtual tissue, and training a first neural network that reconstruct the speed-of-sound distribution image from an input image pair or training a second neural
(Continued)

network that reconstructs the attenuation coefficient distribution image from the input image pair.

12 Claims, 14 Drawing Sheets

(51) Int. Cl.
*A61B 8/15* (2006.01)
*G06N 3/08* (2023.01)

(56) References Cited

U.S. PATENT DOCUMENTS

| | | | | |
|---|---|---|---|---|
| 2015/0141828 | A1* | 5/2015 | Yoshiara | A61B 8/483 |
| | | | | 600/447 |
| 2018/0185005 | A1 | 7/2018 | Sandhu et al. | |
| 2018/0330518 | A1* | 11/2018 | Choi | A61B 8/0866 |
| 2019/0019291 | A1* | 1/2019 | Yousef | G16H 50/30 |
| 2020/0065618 | A1* | 2/2020 | Zhang | G06V 10/82 |
| 2020/0389658 | A1* | 12/2020 | Kim | H04N 19/184 |
| 2021/0077063 | A1* | 3/2021 | Swisher | A61B 8/5207 |
| 2022/0207791 | A1* | 6/2022 | Shi | A61B 6/037 |
| 2022/0262146 | A1* | 8/2022 | Galeotti | G06V 10/82 |

FOREIGN PATENT DOCUMENTS

| | | |
|---|---|---|
| JP | 2021-133123 | 9/2021 |
| KR | 10-2007-0069322 | 7/2007 |
| KR | 10-2013-0080640 | 7/2013 |
| KR | 10-2067340 | 1/2020 |
| WO | 2014/207668 | 12/2014 |

OTHER PUBLICATIONS

Lizuka et al., "Globally and Locally Consistent Image Completion", 2017, ACM transactions on Graphics, vol. 36, No. 4, Article 107 (Year: 2017).*

Li et al., "Convolutional Neural Networks Based Transfer Learning for Diabetic Retinopathy Fundus Image Classification", 2017, 10th International Congress on Image and Signal Processing, BioMedical Engineering and Informatics (Year: 2017).*

Li, Cuiping et al., "In Vivo Breast Sound-Speed Imaging With Ultrasound Tomography", Ultrasound in Med. & Biol., vol. 35, No. 10, pp. 1615-1628, 2009. doi:10.1016/j.ultrasmedbio.2009.05.011.

Alexis Cheng et al., "Deep learning image reconstruction method for limited-angle ultrasound tomography in prostate cancer", Proc. SPIE 10955, Medical Imaging 2019: Ultrasonic Imaging and Tomography, 1095516 (Mar. 15, 2019); https://doi.org/10.1117/12.2512533.

Sanabria, Sergio J, 2018 "Hand-Held Sound-Speed Imaging Based on Ultrasound Reflector Delineation", MICCAI 2016: Medical Image Computing and Computer-Assisted Intervention—MICCAI 2016 pp. 568-576.

Myeong-Gee Kim et al., "Robust Single-Probe Quantitative Ultrasonic Imaging System With a Target-Aware Deep Neural Network," IEEE Transactions on Biomedical Engineering, vol. 68, No. 12, pp. 3737-3747, Dec. 2021, doi: 10.1109/tbme.2021.3086856.

* cited by examiner

METHOD AND APPARATUS FOR QUANTITATIVE IMAGING USING ULTRASOUND DATA

CROSS-REFERENCE TO RELATED APPLICATION

This application claims priority to and the benefit of Korean Patent Application No. 10-2019-0166616 filed in the Korean Intellectual Property Office on Dec. 13, 2019, and Korean Patent Application No. 10-2020-0090261 filed in the Korean Intellectual Property Office on Jul. 21, 2020, the entire contents of which are incorporated herein by reference.

BACKGROUND

(a) Field

The present disclosure relates to an image reconstruction technology using ultrasound.

(b) Description of the Related Art

Since it is difficult to detect a cancer early, periodic examinations are required and the size and characteristics of a lesion should be continuously monitored. Representative imaging equipment for this includes an X-ray, a magnetic resonance imaging (MRI), a computed tomography (CT), and an ultrasound. The X-ray, MRI, and CT have a risk of radiation exposure and a drawback in that the measurement time is long and the cost is too high. In contrast, the ultrasound imaging equipment is safe and relatively inexpensive, and provides a real time image so that a user can obtain desired images while monitoring a lesion in real time.

Presently, a B-mode (brightness mode) imaging system is the most commercially available ultrasound imaging equipment. Since the B-mode imaging system can find a location of the lesion in real time, a user can effectively obtain desired images while monitoring the lesion in real time. In addition, since the B-mode imaging system is safe and relatively inexpensive, the B-mode imaging system has a good accessibility. However, the B-mode imaging system has drawbacks in that the quality of the obtained images may vary according to the proficiency of a user and quantitative characteristics cannot be imaged. That is, since the B-mode technique provides only geometric information of a tissue, the sensitivity and specificity may be low in a differential diagnosis that distinguishes benign tumor and malignant tumor, which are classified by histological characteristics.

Recently, researches to obtain histological information through quantitatively imaging ultrasound characteristics of a tissue have been progressed. Pathological changes in tissues give rise to structural changes in cells, and representative techniques, which perform imaging the change in ultrasound characteristics of the corresponding tissue due to such structural changes, include ultrasound computed tomography (USCT). The ultrasound computed tomography is a reconstruction technique in which the characteristics of a tissue are back-traced through an arrival time or signal strength representing a change of an ultrasound signal inside the tissue. Therefore, through the ultrasound computed tomography, quantitative information, such as a speed-of-sound (SS), an attenuation coefficient AC can be obtained and further a high-resolution quantitative image can be obtained. However, the USCT requires sophisticated transducer modeling, and has a drawback in that the USCT is sensitive to a signal to noise ratio SNR and it is difficult to detect a boundary accurately. In addition, a probe used for USCT should be disposed to enclose an object for obtaining ultrasound data refracted, scattered, and reflected in every direction. Therefore, since USCT should use a probe with a circular structure in many cases, USCT is limited to imaging breast and has a limitation in measuring various organs.

SUMMARY

An embodiment of the present disclosure provides a method and apparatus for quantitatively imaging using ultrasound penetration and reflection characteristics in a tissue. The method and apparatus obtains ultrasound data having penetrated the tissue and ultrasound data reflected from the tissue by using ultrasound probes facing each other Another embodiment of the present disclosure provides a neural network that reconstructs quantitative characteristics included in the ultrasound data having penetrated a tissue by using geometric information obtained from ultrasound data reflected from the tissue as a priori information.

Yet another embodiment of the present disclosure provides a method for reconstructing quantitative image of a tissue by using a trained neural network regardless of a distance between probes, through a region of interest compression that transforms an actual distance between ultrasound probes facing each other into a virtual distance or a virtual depth.

According to an embodiment, a method of operating an image device operated by at least one processor is provided. The method of operating an image device comprises receiving an input of virtual tissues modeled with an arbitrary shape and a quantitative feature, simulating a change in time of flight (TOF) or a signal strength change of ultrasound data having penetrated the virtual tissues modeled with a speed-of-sound distribution or an attenuation coefficient distribution in a first and in a second direction, and creating an image pair representing the TOF change or the signal strength change, creating a speed-of-sound distribution image or an attenuation coefficient distribution image of each of the virtual tissues as a ground truth of an image pair created in the corresponding virtual tissue, and training a first neural network that reconstruct the speed-of-sound distribution image from an input image pair or training a second neural network that reconstructs the attenuation coefficient distribution image from the input image pair, by using training data including an image pair of each virtual tissue and the ground truth.

The image pair may comprise images representing the TOF change of an ultrasound signal in a relationship matrix between transducer channels and receiver channels in a corresponding direction.

The method of operating an image device may further comprise creating a geometric image representing a modeled shape of each virtual tissue, and adding the geometric image of each virtual tissue to the training data.

Training comprises training the first neural network or the second neural network using the geometric image as a priori information.

According to another embodiment, a method of operating an image device operated by at least one processor is provided. The method of operating an image device comprises receiving images created from virtual tissues as training data, and training a neural network with an encoder and a decoder by using the training data. Training the neural network may comprise inputting a TOF image pair or a signal strength image pair included in the training data to the encoder, and training the neural network to minimize a loss between a ground truth and a result that the decoder reconstructs a feature extracted by the encoder. The TOF image pair comprises images representing a TOF change of ultrasound data having penetrated a virtual tissue modeled with a speed-of-sound distribution, in different directions. The signal strength image pair comprises images representing a signal strength change of ultrasound data having penetrated a virtual tissue modeled with an attenuation coefficient distribution, in different directions.

The training data may further comprise speed-of-sound distribution images or attenuation coefficient distribution images of the virtual tissues. Each of the speed-of-sound images may be a ground truth of the TOF images created with a corresponding virtual tissue. Each of the attenuation coefficient distribution images is a ground truth of the signal strength image pair created with the corresponding virtual tissue.

The decoder may comprise a network structure that provides a feature reconstructed at a low resolution and then transformed with a high resolution, through a skip connection.

According to still another embodiment, a method of operating an image device operated by at least one processor is provided. The method of operating an image device comprises receiving input images created from each virtual tissue and a priori information as training data, and training a neural network that reconstructs a quantitative feature of the virtual tissue from the input images under a guidance of the a priori information. The a priori information is a geometric image representing a modeled shape of each virtual tissue. The input images are images representing a TOF change or a signal strength change of ultrasound data having penetrated a virtual tissue modeled with speed-of-sound distribution, in different directions.

Training the neural network may comprise inputting the input images into an encoder of the neural network, and training the neural network to minimize a loss between a ground truth and a result that the decoder reconstructs a feature extracted by the encoder under a guidance of the a priori information.

If the input images are images representing the TOF change, the ground truth may be an image representing a modeled speed-of-sound distribution of each virtual tissue.

If the input images are images representing the signal strength change, the ground truth may be an image representing a modeled attenuation coefficient distribution of each virtual tissue.

According to yet another embodiment, a method of operating an image device operated by at least one processor is provided. The method of operating an image device comprises receiving ultrasound data obtained by a pair of ultrasound probes facing each other, creating a first input image pair representing a TOF change in a measurement target, by using ultrasound-traverse data having penetrated the measurement target among the ultrasound data, through region of interest (ROI) compression that compresses a measured ROI into a virtual ROI, transforming the first input image pair into a second input image pair compressed into the virtual ROI, obtaining a quantitative image reconstructed from the second input image pair, by using a neural network trained to reconstruct a quantitative feature from an input image pair, and restoring the reconstructed quantitative image to the measured ROI.

The ultrasound-traverse data may comprise a first direction traverse data that a second ultrasound probe obtains from an ultrasound signal emitted by a first ultrasound probe of the pair of ultrasound probes, and a second direction traverse data that the first ultrasound probe obtains from an ultrasound signal emitted by the second ultrasound probe of the pair of ultrasound probes.

The first input image pair may comprise a first image representing a TOF change between transducer channels of the first ultrasound probe and receiver channels of the second ultrasound probe, and a second image representing a TOF change between transducer channels of the second ultrasound probe and receiver channels of the first ultrasound probe. The quantitative feature may be a speed-of-sound distribution.

The first input image pair may comprise a first image representing a change in signal strength between transducer channels of the first ultrasound probe and receiver channels of the second ultrasound probe, and a second image representing a change in signal strength between transducer channels of the second ultrasound probe and receiver channels of the first ultrasound probe. The quantitative feature may be an attenuation coefficient distribution.

The method of operating an image device may further comprise creating a geometric image of the measurement target, by using ultrasound-echo data reflected from the measurement target among the ultrasound data, transforming the geometric image to a geometric image compressed into the virtual ROI through the ROI compression, and inputting the compressed geometric image as a priori information of the trained neural network.

The trained neural network may extract a feature of the second input image pair, and, under a guidance of the a priori information, may decode the feature and outputs the quantitative image.

Creating the geometric image may comprise creating a B-mode (brightness-mode) image by using the ultrasound-echo data, and creating the geometric image representing a shape of a target from the B-mode image.

The virtual ROI may be an ROI with a size which is learned by the neural network.

Transforming into the compressed second input image pair may comprise transforming the first input image pair to the second input image pair through a compression matrix, and the compression matrix may include information for compressing an actual ROI formed with an arbitrary distance into the virtual ROI formed with a fixed distance.

By using TOF change images of virtual tissues modeled with speed-of-sound distribution, the neural network may be trained to reconstruct the speed-of-distribution of the corresponding tissues.

By using signal strength change images of virtual tissues modeled with an attenuation coefficient distribution, the neural network may be trained to reconstruct the attenuation coefficient distribution of the corresponding virtual tissues.

The neural network may be trained to reconstruct the speed-of-sound distribution from TOF change images under a guidance of a priori information. The a priori information may be a geometric image of a virtual tissue modeled in an arbitrary shape The TOF change images may be images representing TOF change of the ultrasound data having penetrated the virtual tissue modeled with the speed-of-sound distribution.

The neural network may be trained to reconstruct an attenuation coefficient distribution from signal strength change images under a guidance of a priori information, The a priori information may be a geometric image of a virtual tissue modeled in an arbitrary shape. The signal strength change images may be images representing signal strength change of the ultrasound data having penetrated the virtual tissue modeled with the attenuation coefficient distribution.

According to the embodiment, quantitative features can be imaged by using a pair of ultrasound probes arranged to face each other, instead of using a probe with a circular structure. Thus, the ultrasound computed tomography limited to imaging breast can extend to various organs such as thyroid and pancreas.

According to the embodiment, needless to separately manufacture a probe with a circular structure, features such as a quantitative speed-of-sound distribution can be imaged using an ultrasound probe for B-mode (brightness mode) imaging as it is. According to the embodiment, conventional ultrasound tomography apparatuses can be improved.

According to the embodiment, since quantitative features are reconstructed by using the geometric information of a target as a priori information in a reconstruction network layer of a neural network model, quantitative image can be accurately reconstructed from ultrasound data obtained in noise environment.

According to an embodiment, input images of a neural network are created through a ROI compression that transforms the actual distance between ultrasound probes facing each other into a virtual depth, then the input images are input into a neural network trained with the virtual depth, and images output from the neural network is transformed to the actual distance. Thus, quantitative images can be reconstructed regardless of a distance between ultrasound probes.

DETAILED DESCRIPTION

Figure 1A:
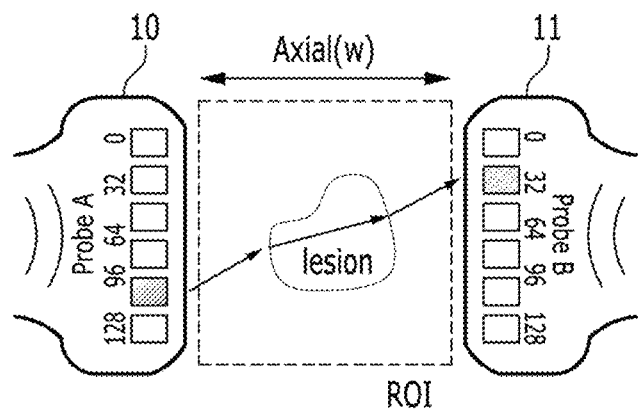
FIGS. 1A, 1B, 1C, 2A, 2B and 2C are diagrams for explaining a method for obtaining ultrasound data using ultrasound probes arranged to face each other.

In the following detailed description, exemplary embodiments of the present disclosure will be described in detail with reference to the accompanying drawings so that those of ordinary skill in the art may easily implement the present disclosure. However, the present disclosure may be implemented in various different forms and is not limited to the embodiments described herein. Accordingly, the drawings and description are to be regarded as illustrative in nature and not restrictive. Like reference numerals designate like elements throughout the specification.

As used herein, unless explicitly described to the contrary, the word "comprise", "include" or "have", and variations such as "comprises", "comprising", "includes", "including", "has" or "having" will be understood to imply the inclusion of stated elements but not the exclusion of any other elements. In addition, the term "unit", "-er", "-or" or "module" described in the specification mean a unit for processing at least one function and operation, and may be implemented by hardware components or software components, and combinations thereof.

A deep neural network of the present disclosure is an artificial intelligence model that learns at least one task and may be implemented as software/program executed in a computing device. The program is stored in a storage medium (non-transitory storage media) and includes instructions for executing operations of the present disclosure by a processor. The program may be downloaded via a network, or sold as a product.

FIGS. 1A, 1B, 1C, 2A, 2B and 2C are diagrams for explaining a method for obtaining ultrasound data using ultrasound probes arranged to face each other.

Referring to FIGS. 1A, 1B, 1C, 2A, 2B and 2B, a pair of ultrasound probes 10 and 11 may be arranged to face each other. From the pair of ultrasound probes, ultrasound data that penetrated a tissue and ultrasonic data reflected from the tissue are obtained. The ultrasound probe_A 10 and the ultrasound probe_B 11 may be fixed by a fixing device to obtain ultrasound data. N piezoelectric elements may be arranged in each of the ultrasound probe_A 10 and the ultrasound probe_B 11. The types of the ultrasound probes 10 and 11 may vary according to the arrangement form of the piezoelectric elements. For example, the ultrasound probes 10 and 11 may be a linear array probe or a curvilinear array probe. Each of the ultrasound probe_A 10 and the ultrasound probe_B 11 may be a phased array probe that generates an ultrasound signal by applying electrical signals to each piezoelectric element at regular time intervals. In the description, each of the piezoelectric elements may be referred to as a channel.

The ultrasound signal emitted from the ultrasound probes 10 and 11 may vary, such as a pulse with a single frequency, a chirp, or a continuous wave. In the description, the emitted ultrasound signal may be exemplified by a pulse.

Referring to FIG. 1A, the ultrasound signal emitted from the ultrasound probe_A 10 penetrates the tissue and then reaches the ultrasound probe_B 11. If there is a lesion that has different quantitative characteristics such as a speed-of-sound and an attenuation coefficient in the tissue, the time of flight (TOF) taken for the emitted ultrasound signal to reach each element in the ultrasound probe_B 11 may be changed. And received signal strength may be changed.

A TOF change $S_{(Tx,Rx)}$ of the emitted signal is defined as a difference between $TOF_{water}$ and $TOF_{obj}$, and can be calculated as in Equation 1. The $TOF_{water}$ is measured in measured in water being a reference and the $TOF_{obj}$ is measured at an object.

$$S_{(Tx,Rx)} = TOF_{obj} - TOF_{water} = \int_{L(Tx,Rx)} s(x,y)dl - \int_{L_0(Tx,Rx)} s_0(x,y)dl \quad \text{Equation 1}$$

In equation 1, L(Tx, Rx) is a pulse propagation path and s(x,y) is a reciprocal of speed-of-sound in a position vector (x,y).

A signal strength $A_{(Tx,Rx)}$ can be calculated as in Equation 2.

$$A_{(Tx,Rx)} = \int_{L(Tx,Rx)} \alpha(x, y) dl = 20\log_{10}\left(\frac{E_{obj}}{E_{water}}\right) \quad \text{Equation 2}$$

In equation 2, α(x,y) is a spatial distribution of the attenuation coefficient. $E_{water}$ and $E_{obj}$ are intensities of received ultrasound during observation of water and the object, respectively.

Figure 1B:
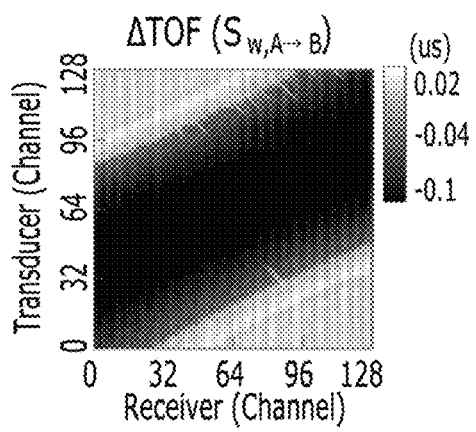
Figure 1C:
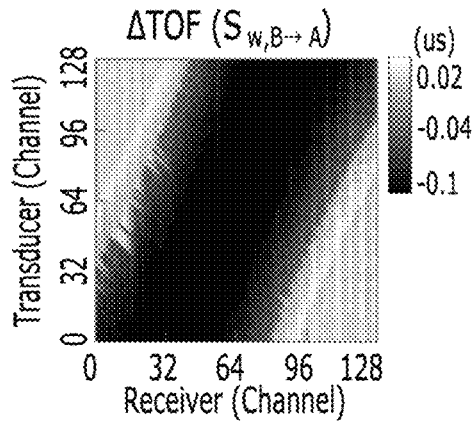

Referring to FIG. 1B, from data which is obtained by the ultrasound probe_B 11 through measuring an ultrasound signal emitted from the ultrasound probe_A 10, a TOF difference ($S_{A \to B}$) is calculated and an image representing the TOF change (ΔTOF) of the ultrasound signal (pulse) in a relationship matrix of transducer channels and receiver channels may be created. Oppositely, referring to FIG. 1C, from data which is obtained by the ultrasound probe_A 10 through measuring an ultrasound signal emitted from the ultrasound probe_B 11, a TOF difference ($S_{B \to A}$) is calculated and an image representing the TOF change (ΔTOF) of the ultrasound signal (pulse) may be created. A pair of TOF images can be input to a neural network that reconstructs quantitative features from the TOF images.

By using the ultrasound data that penetrated the tissue, quantitative features, such as speed-of-sound distribution, of the tissue may be reconstructed. However, since reconstruction is performed with the TOF change and the signal strength, the reconstruction may be sensitive to a signal to noise ratio SNR of the measured data and it may be difficult to accurately detect a boundary of a target.

For the further improvement in quantitative feature reconstruction, geometric information of the target may be used as a priori information. The geometric information may be obtained using the ultrasound data reflected form the tissue.

Figure 2A:
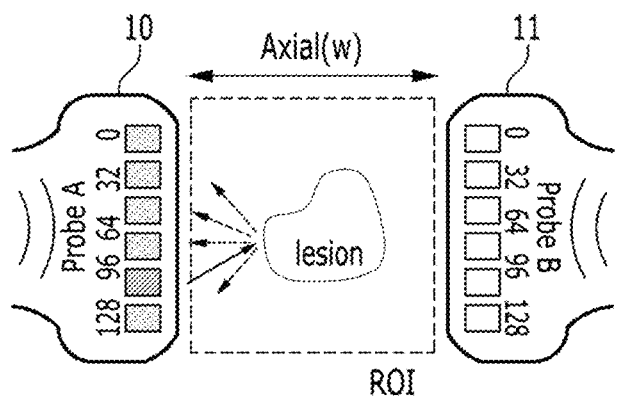

Referring to FIG. 2A, the ultrasound signal emitted from the ultrasound probe_A 10 may be reflected from the tissue and then return to the ultrasound probe_A 10. By using the ultrasound data reflected from the tissue, a location and shape of the target within the tissue can be reconstructed, which may be imaged with a B-mode (brightness-mode) technique. A B-mode image may be an image created with amplitude obtained through envelope detection of a waveform generated from the reflected ultrasound data.

Figure 2B:
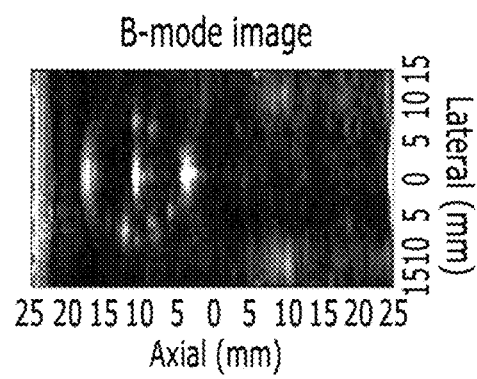

Referring to FIG. 2B, since the B-mode image includes geometric information, a geometric image representing the boundary of the target can be created from the B-mode image.

Figure 2C:
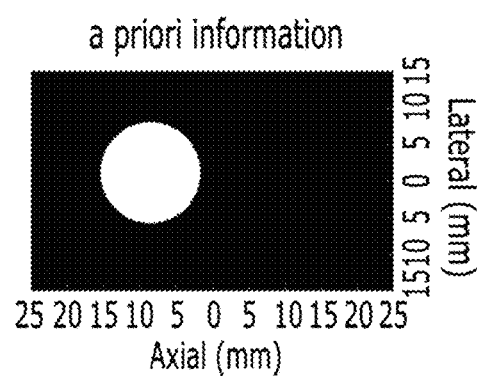

Referring to FIG. 2C, the geometric image may be a binary image of the B-mode image or a segmented image divided into regions. The geometric image may be input to a decoder of a neural network as a priori information.

A neural network that uses the geometric information of the target as a priori information can securely generate a quantitative image even in a noise environment and can rapidly reconstruct the quantitative features inside the target. The neural network may be referred to as a QIP-Net (quantitative imaging network incorporating a priori information). Hereinafter, a device and method for quantitative imaging will be described in detail.

Figure 3:
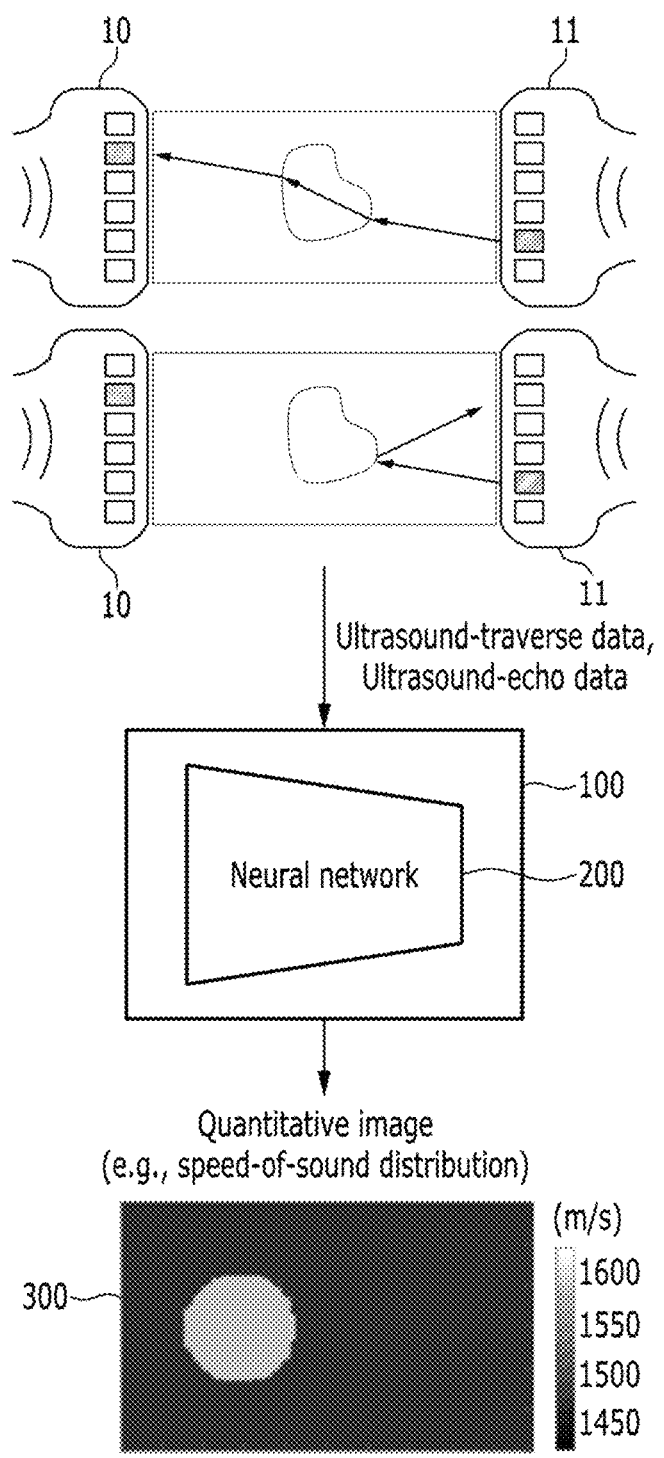
FIG. 3 is a diagram for conceptually explaining an ultrasound imaging device according to an embodiment.

FIG. 3 is a diagram for conceptually explaining an ultrasound imaging device according to an embodiment.

Referring to FIG. 3, an imaging device 100 is a computing device operated by at least one processor. The imaging device 100 receives ultrasound data obtained by an ultrasound probe_A 10 and an ultrasound probe_B 11. The imaging device 100 images quantitative features of a tissue using a neural network 200 with an encoder-decoder structure. The imaging device 100 may create, for example, a speed-of-sound (SS) distribution image 300. Depending on training data of the neural network 200, the imaged quantitative features may be determined as a speed-of-sound (SOS) or an attenuation coefficient (AC).

In the description, in order to distinguish the obtained ultrasound data, the ultrasound data that penetrated the tissue is referred to as ultrasound-traverse data and the ultrasound data reflected from the tissue is referred to as ultrasound-echo data. The ultrasound-traverse data may be obtained in a predetermined first mode (e.g., tomography mode) of a probe and the ultrasound-echo data may be obtained in a predetermined second mode (e.g., B-mode) of the probe.

In the case of tomography mode, transmission and reception (Tx/Rx) may be set so that the ultrasound probe_A 10 emits an ultrasound signal and then the ultrasound probe_B 11 receives ultrasound-traverse data, or so that the ultrasound probe_B 11 emits an ultrasound signal and then the ultrasound probe_A 10 receives the ultrasound-traverse data. For example, when each of the ultrasound probe_A 10 and the ultrasound probe_B 11 is composed of 128 piezoelectric elements, 256 piezoelectric elements sequentially emit an ultrasound signal, and the signal having penetrated the tissue may be recorded by the 128 piezoelectric elements of the probe located on the opposite side with a sampling speed of 62.5 MHz.

In the case of B-mode, transmission and reception (Tx/Rx) may be set so that the ultrasound probe_A 10 emits an ultrasound signal and then receives ultrasound-echo data, or so that the ultrasound probe_B 11 emits an ultrasound signal and then receives the ultrasound-echo data.

The imaging device 100 mounts a trained neural network 200. The neural network 200 is trained to receive an input of an image created with ultrasound-traverse data and to reconstruct quantitative features included in the input image. At this time, the neural network 200 may be trained to reconstruct the quantitative features by receiving a geometric image as a priori information. A neural network that receives a priori information and reconstructs quantitative features may be referred to as a quantitative imaging network incorporating a priori information neural network (QIP-Net), and a neural network that reconstructs quantitative features without a priori information may be referred to as a quantitative imaging neural network (QI-Net) separately.

Learning of the neural network 200 may be performed in a separate device, but it will be described that the imaging device 100 trains the neural network 200 for convenience of explanation.

Figure 4:
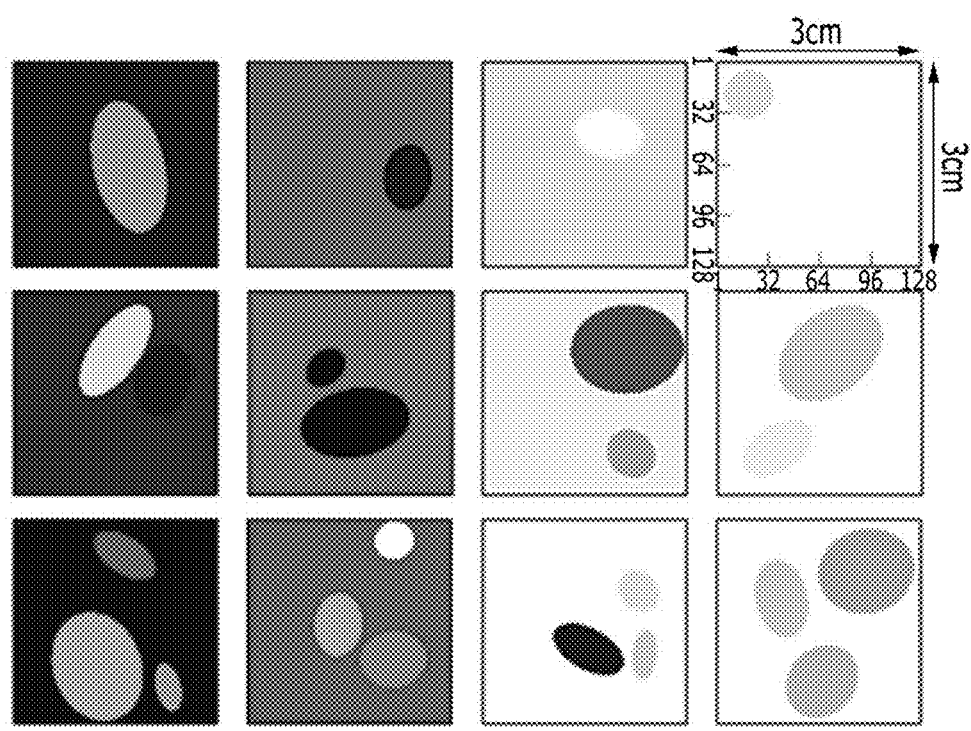
FIG. 4 and FIG. 5 are diagrams for explaining a method of generating training data for a neural network according to an embodiment.
Figure 5:
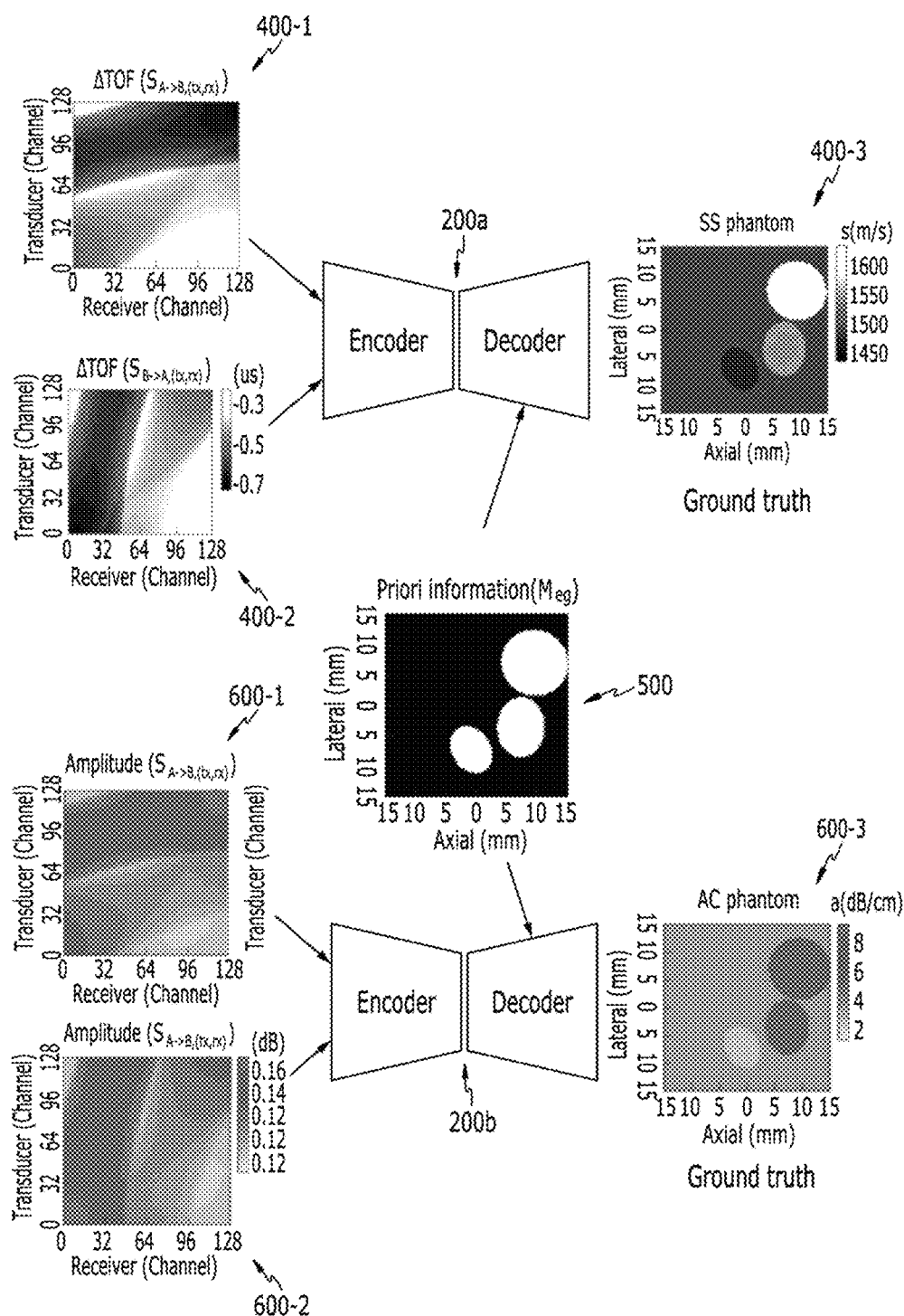

FIG. 4 and FIG. 5 are diagrams for explaining a method of generating training data for a neural network according to an embodiment.

Referring to FIG. 4, training data of a neural network 200 is generated through modeling various tissues. The modeled tissues (virtual tissues) are variously generated to have arbitrary shapes and quantitative features, and at least one ellipse corresponding to, for example, an organ or a lesion may be randomly placed in the background. Here, soft tissues may be modeled.

The background and a speed-of-sound/attenuation coefficient of the ellipse may be selected in a range representing general quantitative features of the tissue (e.g., 1434 m/s to 1634 m/s, and 0 dB/cm to 10 dB/cm). Each tissue may be modeled as a fixed region of interest (e.g., 3 cm×3 cm).

Referring to FIG. 5, in order to train a neural network 200a imaging a speed-of-sound distribution in a tissue, the imaging device 100 may generate training data which simulates each tissue shown in FIG. 4 with a TOF change (ΔTOF) model as in Equation 1.

For a tissue whose quantitative features are modeled, the imaging device 100 may simulate the TOF change (ΔTOF) for a signal transmitted from transducer channels of a probe_A to receiver channels of a probe B. The imaging device 100 may generate a TOF image 400-1 representing the ΔTOF (SAB) of an ultrasound signal (pulse) in a relationship matrix of the transducer channels and the receiver channels. The imaging device 100 may simulate a case where the transmission probe and the reception probe are reversed and then may generate a TOF image 400-2 representing ΔTOF (SBA). The imaging device 100 may generate a speed-of-sound distribution image 400-3 representing the speed-of-sound distribution of the corresponding tissue as a ground truth label.

The neural network 200a receives a pair of TOF images 400-1 and 400-2 and may learn to reconstruct a speed-of-sound distribution image with the smallest difference from the speed-of-sound distribution image 400-3 being the ground truth label.

Meanwhile, in order to train a neural network 200b for imaging an attenuation coefficient distribution in the tissue, the imaging device 100 may generate training data which simulates each tissue shown in FIG. 4 with a received signal strengths model as in Equation 2.

For the tissue whose quantitative features are modeled, the imaging device 100 may simulate a signal intensity change for a signal transmitted from the probe_A to the probe_B, and may generate an image 600-1 representing the signal strength change ($A_{A \rightarrow B}$) of an ultrasound signal in a relationship matrix between transducer channels and receiver channels. The imaging device 100 may simulate a case where the transmission probe and the reception probe are reversed and then may generate an image 600-2 representing a signal strength change (ABA). The imaging device 100 may generate an attenuation coefficient distribution image 600-3 representing the attenuation coefficient distribution of the corresponding tissue as a ground truth label.

The neural network 200b receives a pair of signal strength images 600-1 and 600-2 and can learn to reconstruct the attenuation coefficient distribution image which has the smallest difference from the attenuation coefficient distribution image 600-3 being the ground truth label.

When the neural network 200a and/or neural network 200b is composed of a QIP-Net that reconstructs the quantitative features with a priori information, the imaging device 100 generates a geometric image 500 representing shapes of ellipses placed in the corresponding tissue, and may use the geometric image 500 as training data. The geometric image 500 is inputted into a decoder of the QIP-Net as a priori information. When reconstructing the features output from an encoder, the decoder uses the shape of the target which has been input as a priori information. Thus, the decoder can accurately and securely reconstruct the quantitative features of a target.

Though it is described that a TOF image pair is input as input images of the neural network in the description, an attenuation coefficient image pair may be input as the input images of the neural network or a TOF image pair and an attenuation coefficient image pair may be input as the input images of the neural network.

Figure 6:
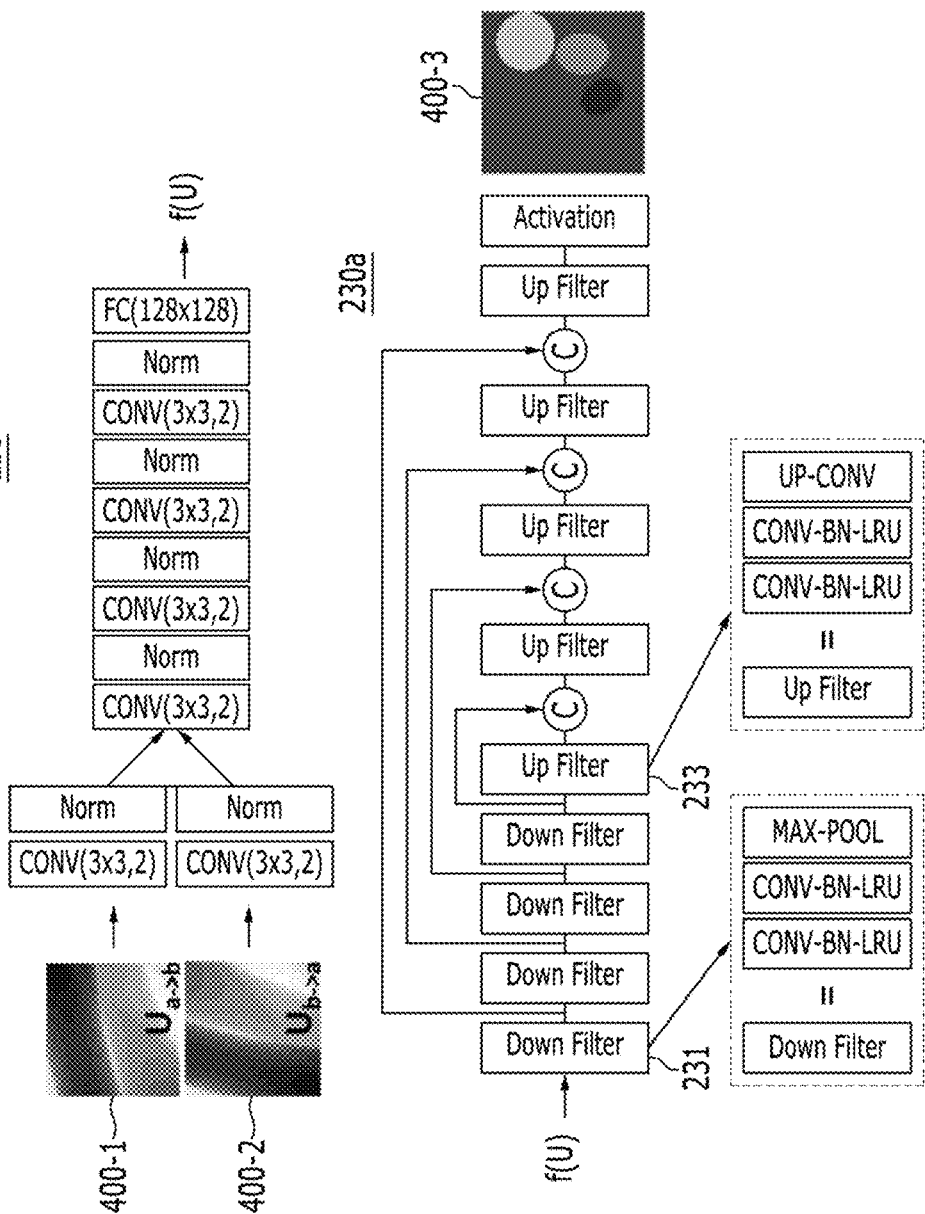
FIG. 6 is a configuration diagram of a QI-Net according to an embodiment.
Figure 7:
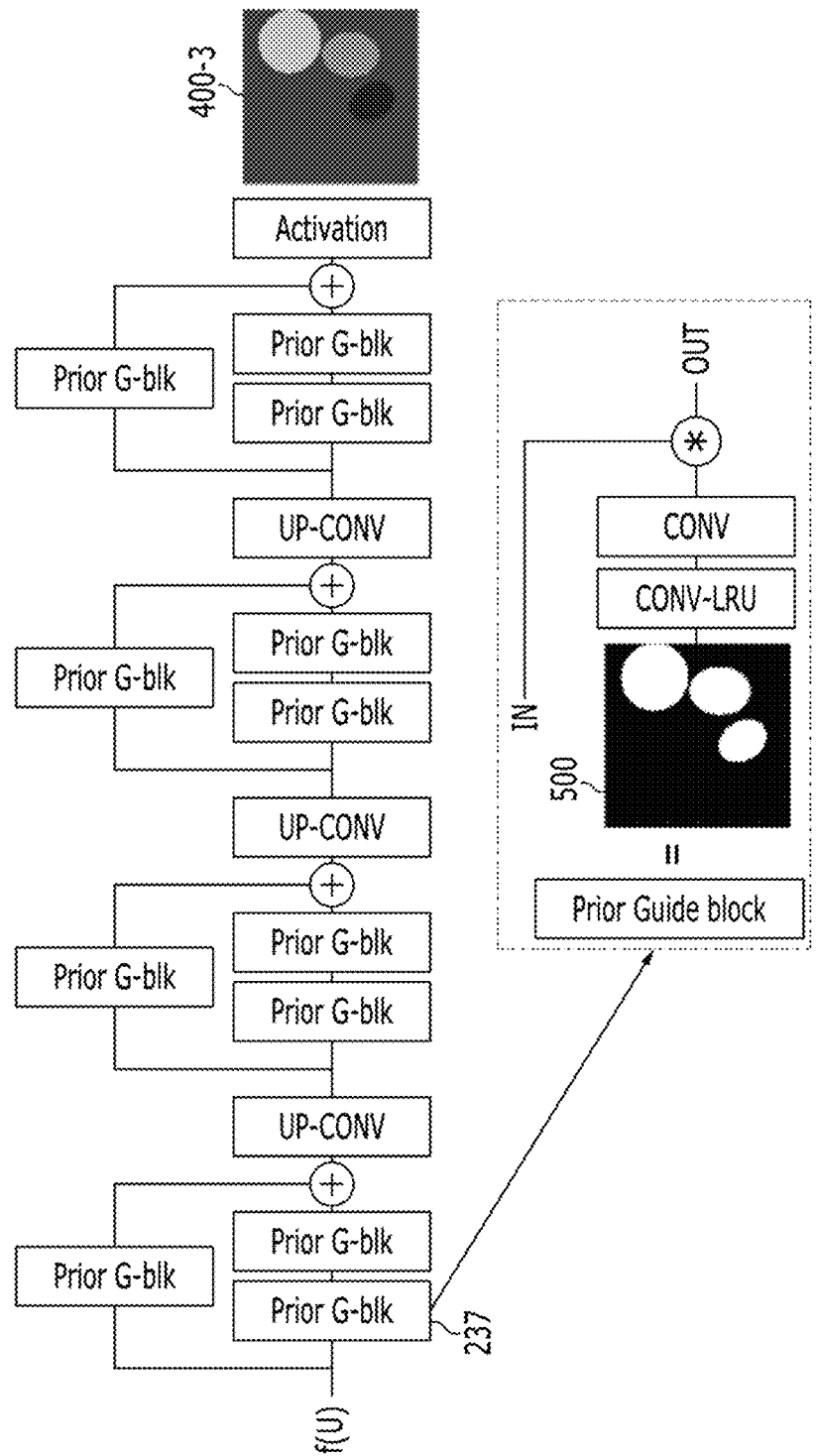
FIG. 7 is a configuration diagram of a QIP-Net according to another embodiment.

FIG. 6 is a configuration diagram of a QI-Net according to an embodiment, and FIG. 7 is a configuration diagram of a QIP-Net according to another embodiment.

Referring to FIG. 6 and FIG. 7, a neural network 200 for ultrasound imaging is an artificial intelligence model capable of learning at least one task and may be implemented as software/program executed in a computing device. The neural network 200 includes an encoder that encodes features of input images U, and a decoder that decodes (reverse rendering) a feature map f(U) generated by the encoder to reconstruct a quantitative image. In the description, it is described that the speed-of-sound distribution image 400-3 is reconstructed, and the neural network structure may be variously designed.

The encoder 210 receives a pair of TOF images 400-1 and 400-2 representing the TOF change between two facing ultrasound probes.

The encoder 210 includes convolution layers for extracting features of the TOF images, and may output the feature map f(U) through a fully connected layer FC. For example, the encoder 210 can extract features of the input through convolution filtering (Cony, 3×3 Kernel size, 2×2 stride), normalization (Norm), and activation function (Leaky ReLU, LRU).

The output f(U) of the encoder 210 is input into the decoder. The decoder may or may not receive a priori information, which may change the structure of the decoder.

As shown in FIG. 6, a neural network where a decoder 230a reconstructs the feature f(U) transmitted from the encoder 210 without a priori information may be referred to as a QI-Net. As shown in FIG. 7, a neural network where a decoder 230b reconstructs the feature f(U) transmitted from the encoder 210 using a priori information may be referred to as a QIP-Net.

Referring to FIG. 6, the decoder 230a that reconstructs without a priori information may configure a U-Net connection path to improve the reconstruction performance.

The decoder 230a downsamples the feature map f(U) with a low resolution (low-level) through a downsampling block 231, and then gradually upsamples the feature map f(U) with a high resolution (high-level) through an upsampling block 233 to output the speed-of-sound distribution image 400-3. In this case, through skip connections of U-Net, the decoder 230a may provide features reconstructed at the low resolution as transformed with the high resolution. That is, skip-connected features may be concatenated (concatenation, C).

The downsampling block 231 extracts features through convolution filtering (CONV), normalization (Norm), and activation function (LRU), and then may perform max-pooling (MAX-POOL). The upsampling block 233 may extract features through convolution filtering (CONV), normalization (Norm), and activation function (LRU), and then may perform up-convolution (UP-CONV).

Referring to FIG. 7, the decoder 230b may reconstruct the quantitative image 400-3 from the feature map f(U) by using a geometric image 500 as a priori information. Through a prior guide block (Prior G-blk) 237, the decoder 230b may combine the input geometric image 500 with an encoded feature IN to transmit to an output OUT. Through a residual connection, the decoder 230b may be configured such that the encoded features pass through a series of the prior guide blocks 237.

A neural network where the decoder 230a reconstructs the feature map f(U) transmitted from the encoder 210 without a priori information as shown in FIG. 6 may be referred to as a QI-Net. A neural network where the decoder 230b reconstructs the feature f(U) transmitted from the encoder 210 using a priori information as shown in FIG. 7 may be referred to as a QIP-Net.

The QI-Net that does not use a priori information can perform learning to minimize reconstruction loss by using a loss function G* as in Equation 3. That is, the QI-Net is trained to minimize a difference between an output G(U) inferred from an input U and a ground truth Y.

$$G^* = \underset{G}{\operatorname{argmin}} \mathbb{E}_{U,Y}[\|Y - G(U)\|^2] \qquad \text{Equation 3}$$

The QIP-Net using a priori information may perform learning to minimize the reconstruction loss by using a loss function G* as in Equation 4. That is, the QIP-Net is trained so that a difference between an output G (U, $M_{eg}$) inferred from the input U through the guidance of a priori information $M_{eg}$ and the ground truth Y is minimized $$G^* = \underset{G}{\operatorname{argmin}} \mathbb{E}_{U,Y,M_{eg}}[\|Y - G(U, M_{eg})\|^2] \qquad \text{Equation 4}$$

Figure 8:
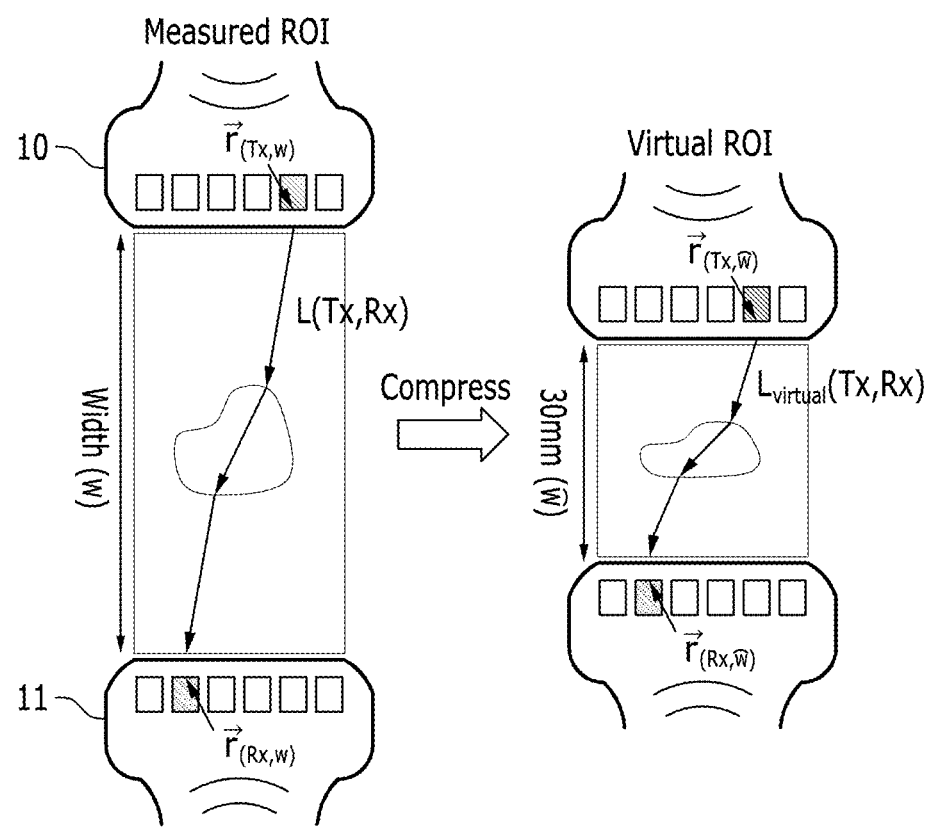
FIG. 8 is a diagram for explaining the transformation of measured ultrasound data into a virtual region of interest according to an embodiment
Figure 9:
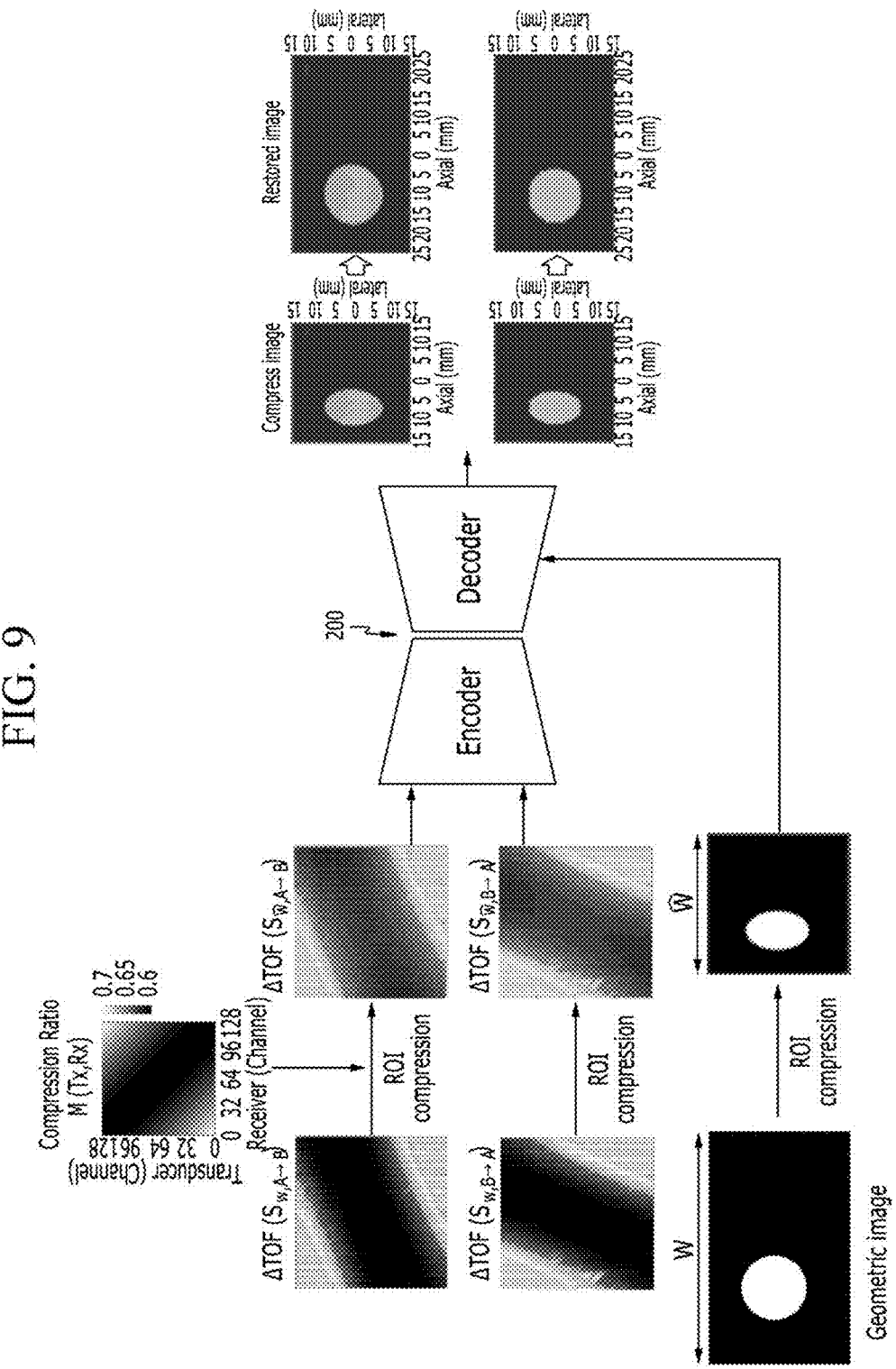
FIG. 9 is a diagram for explaining quantitative image reconstruction through region of interest compression according to an embodiment.

FIG. 8 is a diagram for explaining the transformation of measured ultrasound data into a virtual region of interest (ROI) according to an embodiment, and FIG. 9 is a diagram for explaining quantitative image reconstruction through ROI compression according to an embodiment.

Referring to FIG. 8, when ultrasound data is measured by using ultrasound probes 10 and 11 facing each other, a distance w between the probes may be changed depending on a measurement target. However, since a neural network 200 learns with an ROI in which the distance between probes is fixed, when an input image is created using the measured ultrasound data as it is, the restoration performance deteriorates.

In order to solve this problem, the imaging device 100 transforms the actual distance w between the ultrasound probes into a virtual distance $\hat{w}$ of a virtual ROI through ROI compression. The virtual ROI may be an ROI learned by the neural network 200.

The imaging device 100 may transform ultrasound data $U_w$(Tx, Rx) measured at an arbitrary distance w into a value in the virtual ROI using a compression matrix $M_w$(Tx, Rx).

The imaging device 100 may compress the measured ROI into the virtual ROI as in Equation 5. The compression matrix $M_w$(Tx,Rx) may be defined as in Equation 6. In equation 5, u(x,y) is quantitative information (quantitative profile) and r is a position vector.

$$U_{\hat{w}}(Tx, Rx) = \qquad \text{Equation 5}$$
$$\int_{L_{\hat{w}}} u(x, y) dl_{\hat{w}} = \int_{L_w} \frac{u(x, y)}{M_w(Tx, Rx)} dl_w = \frac{U_w(Tx, Rx)}{M_w(Tx, Rx)}$$

$$M_w(Tx, Rx) = \frac{L_{\hat{w}}(Tx, Rx)}{L_w(Tx, Rx)} \approx \frac{|\vec{r}_{(Tx,\hat{w})} - \vec{r}_{(Rx,\hat{w})}|}{|\vec{r}_{(Tx,w)} - \vec{r}_{(Rx,w)}|} \qquad \text{Equation 6}$$

Referring to FIG. 9, the imaging device 100 creates TOF images, ΔTOF ($S_{w, A \to B}$) and ΔTOF ($S_{w, B \to A}$) representing TOF changes by using measured ultrasound-traverse data. The imaging device 100 transforms the TOF images, ΔTOF ($S_{w, A \to B}$) and ΔTOF ($S_{w, B \to A}$) into a virtual ROI by using the compression matrix. The TOF images transformed into the virtual ROI are input to the trained neural network 200. The compression matrix may be an image including a compression ratio between transducer channels and receiver channels.

The imaging device 100 generates a geometric image of an actual distance w by using the measured ultrasound-traverse data. The imaging device 100 transforms the geometric image of the actual distance w into a geometric image of the virtual distance $\hat{w}$, by using the compression matrix. The geometric image transformed into the virtual ROI is input to a decoder of the trained neural network 200.

The imaging device 100 obtains a speed-of-sound distribution image output from the trained neural network 200, and restores a compressed speed-of-sound distribution image to a speed-of-sound distribution image of the actual distance w.

Figure 10:
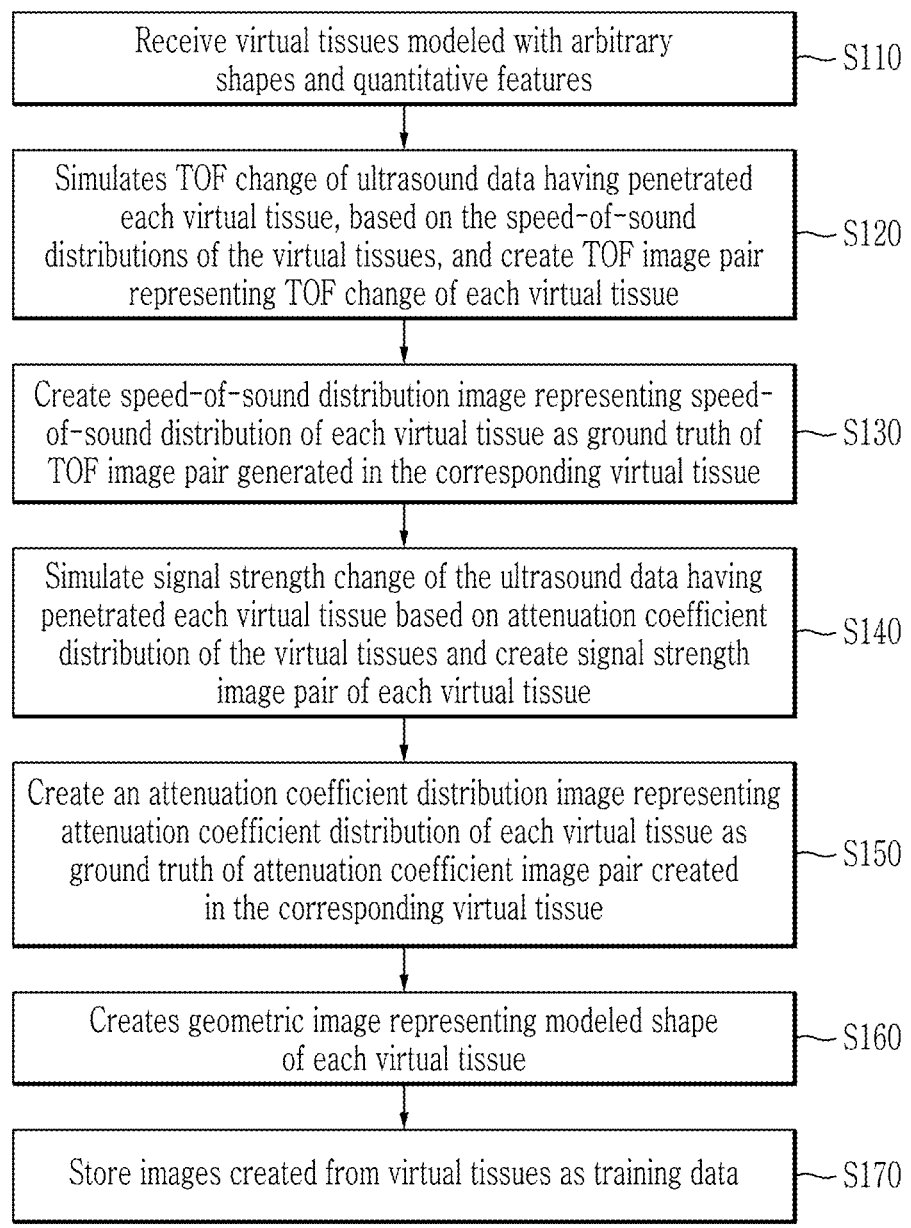
FIG. 10 is a flowchart of a method for generating training data of a neural network according to an embodiment.

FIG. 10 is a flowchart of a method for generating training data of a neural network according to an embodiment.

Referring to FIG. 10, the imaging device 100 receives virtual tissues modeled with arbitrary shapes and quantitative features (S110). The virtual tissues are variously generated to have arbitrary shapes and quantitative features. For example, as described in FIG. 4, at least one ellipse may be randomly placed in a background of a certain size. The speed-of-sound/attenuation coefficient of the background and ellipse may be selected so as to represent the general quantitative features of the virtual tissues.

The imaging device 100 simulates the TOF change (ΔTOF) of ultrasound data having penetrated each virtual tissue, based on the speed-of-sound distributions of the virtual tissues, and creates a TOF image pair representing the TOF change of each virtual tissue (S120). The imaging device 100 may create a pair of TOF images representing a TOF change of the signal having penetrated the tissue in a first direction and a TOF change of the signal having penetrated the tissue in a second direction, according to the quantitative features of each virtual tissue.

The imaging device 100 creates a speed-of-sound distribution image representing the speed-of-sound distribution of each virtual tissue as a ground truth of the TOF image pair created in the corresponding virtual tissue (S130).

The imaging device 100 simulates a signal strength change of the ultrasound data having penetrated each virtual tissue based on the attenuation coefficient distribution of the virtual tissues and creates a signal strength image pair of each virtual tissue (S140).

The imaging device 100 creates an attenuation coefficient distribution image representing the attenuation coefficient distribution of each virtual tissue as a ground truth of an attenuation coefficient image pair created in the corresponding virtual tissue (S150).

The imaging device 100 creates a geometric image representing the modeled shape of each virtual tissue (S160).

The imaging device 100 stores images created from the virtual tissues as training data (S170). The training data may include the TOF image pair and the speed-of-sound distribution image, the signal strength image pair and the attenuation coefficient distribution image, and the geometric image. Images selected from the training data depending on a training task of a neural network may be used for actual training.

Figure 11:
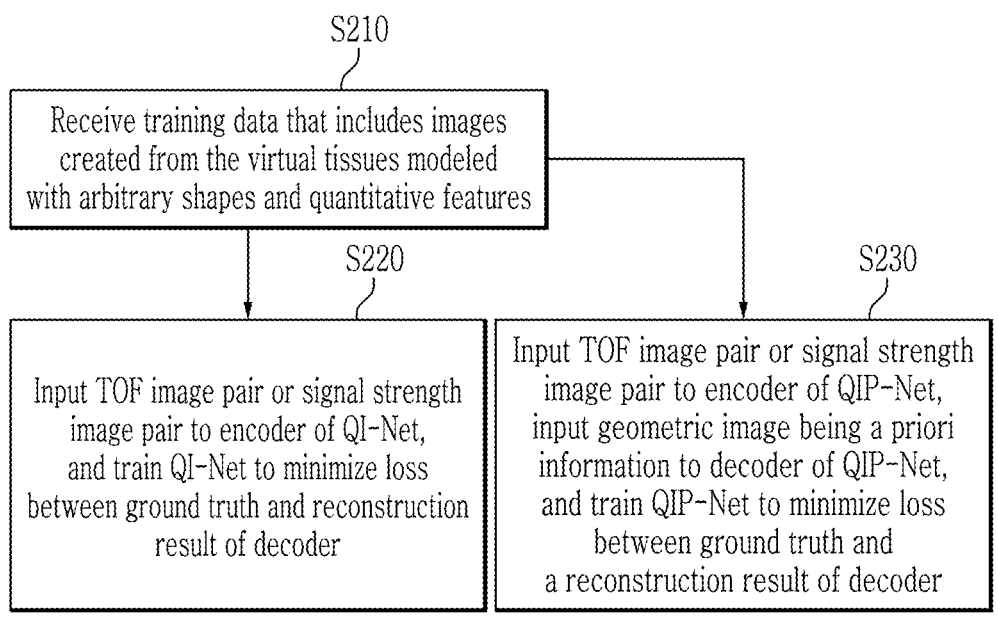
FIG. 11 is a flowchart of a neural network learning method according to an embodiment.

FIG. 11 is a flowchart of a neural network training method according to an embodiment.

Referring to FIG. 11, the imaging device 100 receives training data including images created from the virtual tissues (S210). The virtual tissues are modeled with arbitrary shapes and quantitative features. The training data may include a TOF image pair and a speed-of-sound distribution image being a ground truth of the TOF image pair. The training data may include a signal strength image pair and an attenuation coefficient distribution image being a ground truth of the signal strength image pair. The training data may include a geometric image.

The imaging device 100 inputs the TOF image pair or the signal strength image pair to an encoder of the QI-Net, and trains the QI-Net to minimize a loss between the ground truth and a reconstruction result of decoder (S220). The QI-Net includes an encoder that encodes features of the input images and a decoder that reconstructs a quantitative image by decoding features extracted by the encoder. The structure of the neural network may be designed variously. For example, the decoder of the QI-Net may be configured with a U-Net that reconstructs features at a low resolution and provide the reconstructed features after transforming with a high resolution, through skip connections as shown in FIG. 6.

The imaging device 100 inputs the TOF image pair or the signal strength image pair to the encoder of the QIP-Net, inputs a geometric image being a priori information to the decoder of the QIP-Net, and then trains the QIP-Net to minimize a loss between a ground truth and a reconstruction result of decoder (S230). The QIP-Net also includes an encoder that encodes features of input images and a decoder that reconstructs a quantitative image through decoding features extracted by the encoder. The structure of the neural network may be designed variously. For example, the decoder of the QIP-Net includes a prior guide block that combines input geometric image with encoded features as shown in FIG. 7. Particularly, it may be configured so that the encoded features pass through a series of prior guide blocks via residual connections.

Figure 12:
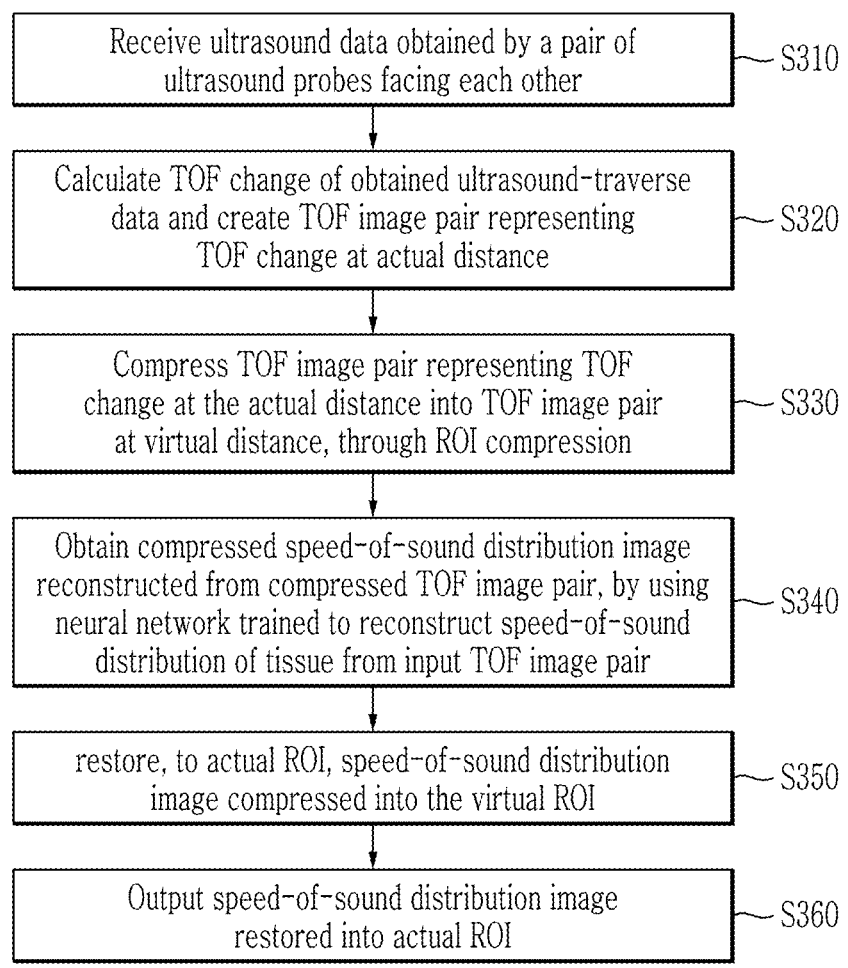
FIG. 12 is a flowchart of an imaging method according to an embodiment.

FIG. 12 is a flowchart of an imaging method according to an embodiment.

Referring to FIG. 12, the imaging device 100 receives ultrasound data obtained by a pair of ultrasound probes facing each other (S310). The two ultrasound probes are arranged to face each other with an actual distance. Further, since the distance is changed depending on the measurement target, ROI of the ultrasound probe pair is changed according to the measurement target. The obtained ultrasound data includes ultrasound-traverse data. The obtained ultrasound data may further include ultrasound-echo data obtained by the ultrasound probe having emitted an ultrasound signal.

The imaging device 100 calculates a TOF change ($\Delta$TOF) of the obtained ultrasound-traverse data and creates a TOF image pair representing the TOF change at an actual distance (S320). The imaging device 100 may create the TOF image representing the $\Delta$TOF by using ultrasound-traverse data obtained from penetrating a tissue in a first direction and ultrasound-traverse data obtained from penetrating the tissue in a second direction.

Through ROI compression, the imaging device 100 compresses the TOF image pair representing the TOF change at the actual distance into a TOF image pair at a virtual distance (S330). The imaging device 100 may transform the ultrasound data measured at the actual distance w into a value in a virtual ROI, by using a compression matrix. The actual distance w is an actual ROI measured by the probes and is variable, and the virtual distance is the virtual ROI learned by the neural network and is fixed.

The imaging device 100 obtains a compressed speed-of-sound distribution image which is reconstructed from the compressed TOF image pair, by using a neural network trained to reconstruct the speed-of-sound distribution of the tissue from the input TOF image pair (S340).

The imaging device 100 restores, to the actual ROI, the speed-of-sound distribution image compressed into the virtual ROI (S350).

The imaging device 100 outputs the speed-of-sound distribution image restored into the actual ROI (S360).

Meanwhile, when using a QIP-Net that reconstructs a speed-of-sound distribution using a geometric image as a priori information, the imaging device 100 creates a B-mode image using the obtained ultrasound-echo data and creates a geometric image representing a shape (boundary) of a target from the B-mode image. In addition, the imaging device 100 may create a geometric image compressed into a virtual ROI through the ROI compression, and may input the compressed geometric image as a priori information of the QIP-Net neural network.

The imaging device 100 may restore not only the speed-of-sound distribution but also various quantitative features. For example, the imaging device 100 may calculate a signal strength change in an ROI from the obtained ultrasound-traverse data and, through ROI compression, may compress a signal strength image pair at the actual distance into a signal strength image pair at a virtual distance. The imaging device 100 may obtain a compressed attenuation coefficient image restored from the compressed signal strength image pair, by using a neural network trained to restore an attenuation coefficient distribution of a tissue from the input signal strength image pair. The imaging device 100 may restore, to the actual ROI, the compressed attenuation coefficient distribution into the virtual ROI and then may output a restored attenuation coefficient.

Figure 13A:
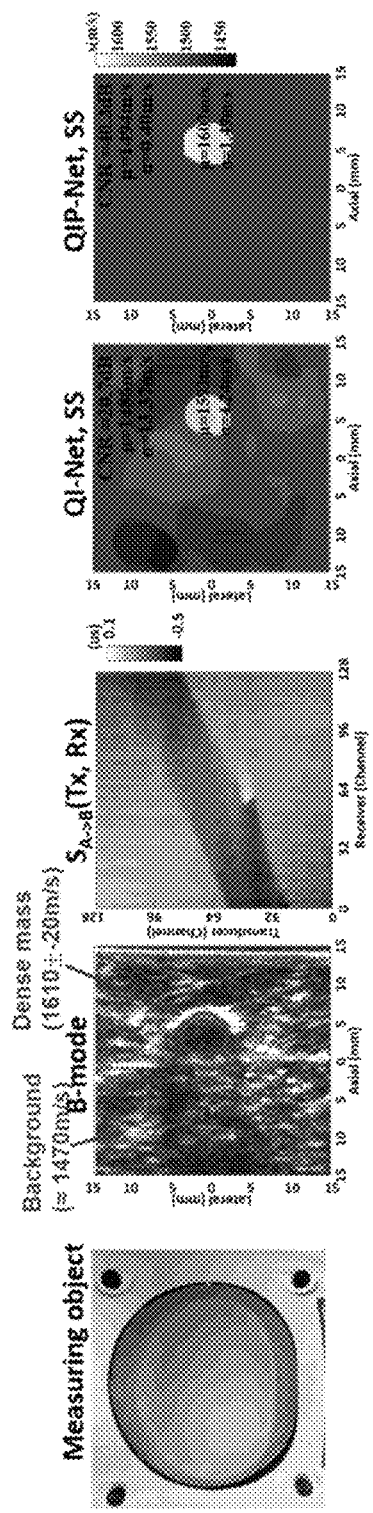
FIGS. 13A and 13B are results of quantitative image reconstruction using a neural network according to an embodiment.
Figure 13B:
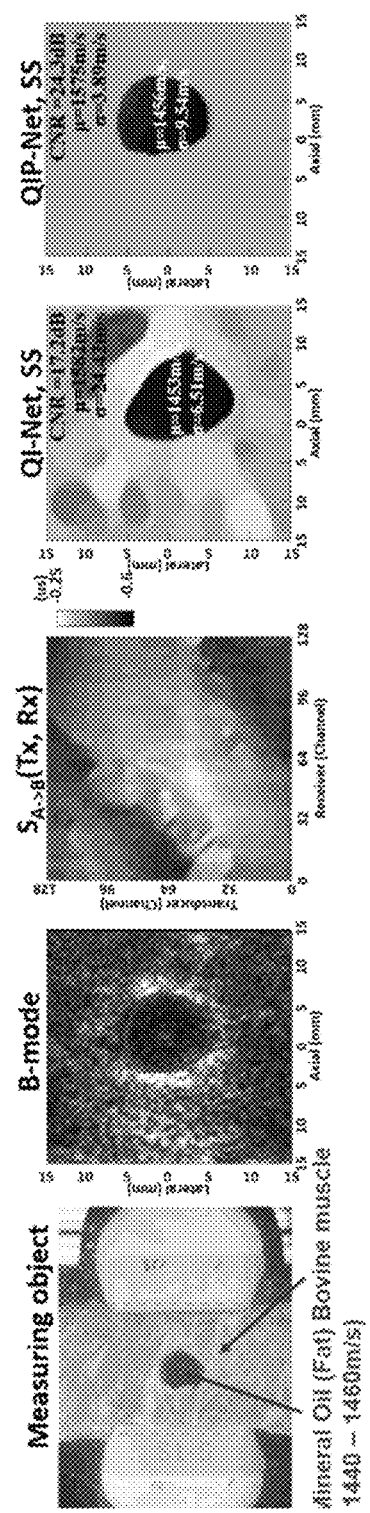

FIGS. 13A and 13B are results of quantitative image reconstruction using a neural network according to an embodiment.

FIG. 13A shows a quantitative image reconstruction result using a breast phantom with an object mimicking a tumor. The images shown in FIG. 13A are results that the imaging device 100 reconstructs a quantitative speed-or-sound (SS) distribution image based on ultrasound data obtained from the breast phantom with the trained neural network QI-Net and QIP-Net.

FIG. 13B shows a quantitative image reconstruction result using bovine muscle with objects mimicking a lesion. The images shown in FIG. 13B are results that the imaging device 100 reconstructs a quantitative speed-or-sound (SS) distribution image based on ultrasound data obtained from the bovine muscle with the trained neural network QI-Net and QIP-Net.

It can be seen that the QIP-Net using the geometric information as a priori information has a higher reconstruction performance than the QI-Net but both of the QIP-Net and QI-Net can securely reconstruct quantitative features.

Figure 14:
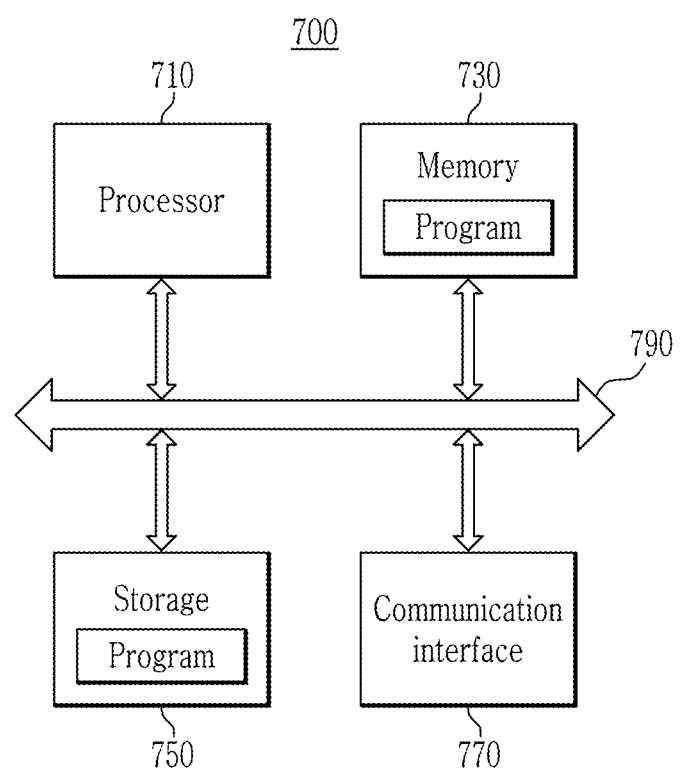
FIG. 14 is a configuration diagram of a computing device according to an embodiment.

FIG. 14 is a configuration diagram of a computing device according to an embodiment.

Referring to FIG. 14, an imaging device 100 may be a computing device 700 operated by at least one processor, and may be connected with ultrasound probes 10 and 11 or a device providing data obtained by the ultrasound probes 10 and 11.

The computing device 700 may include at least one processor 710, a memory 730 for loading a program executed by the processor 710, a storage 750 for storing programs and various data, a communication interface 770, and a bus 790 connecting them. In addition, the computing device 700 may further include various elements. When the program is loaded on the memory 730, the program may include instructions that make the processor 710 to perform methods/operations according to various embodiments of the present disclosure. That is, the processor 710 may perform methods/operations according to various embodiments of the present disclosure by executing instructions. The instructions are a series of computer readable instructions grouped by a function, which refers to elements of the computer program and being executed by a processor.

The processor 710 controls the overall operation of each elements of the computing device 700. Processor 710 may include at least one of a central processing unit (CPU), a micro processor unit (MPU), a micro controller unit (MCU), a graphic processing unit (GPU), or any type of processor well known in the art to which the present disclosure pertains. Further, the processor 710 may perform calculations for at least one application or program to execute methods/operations according to various embodiments of the present disclosure.

The memory 730 stores various data, instructions and/or information. The memory 730 may load at least one program from the storage 750 in order to perform methods/operations according to various embodiments of the present disclosure. The memory 730 may be implemented with a volatile memory such as RAM, but the technical range of the present disclosure is not limited thereto.

The storage 750 may store programs non-temporarily. The storage 750 may include a non-volatile memory, such as a read only memory (ROM), an erasable programmable ROM (EPROM), an electrically erasable programmable ROM (EEPROM), a flash memory, or any form of computer-readable recording medium well known in the art to which the present disclosure pertains.

The communication interface 770 supports wired/wireless communication of the computing device 700. To this end, the communication interface 770 may include a communication module well known in the technical field of the present disclosure.

The bus 790 provides a communication function between the elements of the computing device 700. The bus 790 may be implemented as various forms of buses, such as an address bus, a data bus, and a control bus.

As described above, according to the embodiment, quantitative features can be imaged by using a pair of ultrasound probes arranged to face each other, instead of using a probe with a circular structure. Thus, the ultrasound computed tomography limited to imaging breast can extend to various organs such as thyroid and pancreas.

According to the embodiment, needless to separately manufacture a probe with a circular structure, features such as a quantitative speed-of-sound distribution can be imaged using an ultrasound probe for B-mode (brightness mode) imaging as it is. According to the embodiment, conventional ultrasound tomography apparatuses can be improved.

According to the embodiment, since quantitative features are reconstructed by using the geometric information of a target as a priori information in a reconstruction network layer of a neural network model, quantitative image can be accurately reconstructed from ultrasound data obtained in noise environment.

According to the embodiment, since the neural network is trained after creating input images for the neural network through ROI compression that transforms an actual distance between ultrasound probes facing each other to a virtual distance, a quantitative image can be restored from ultrasound data measured at an arbitrary distance of a probe.

The embodiments of the present disclosure described above are not implemented through only the apparatus and the method, but may also be implemented through a program that realizes functions corresponding to the configuration of the embodiments of the present disclosure or a recording medium on which the program is recorded.

While this disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A method of operating an image device operated by at least one processor, the method comprising:

receiving ultrasound data obtained by a pair of ultrasound probes facing each other, the pair of ultrasound probes comprising a first ultrasound probe and a second ultrasound probe;

creating a first input image pair representing a time of flight (TOF) change in a measurement target, by using ultrasound-traverse data having penetrated the measurement target among the ultrasound data, the first input image pair comprising a first image representing a TOF change between transducer channels of the first ultrasound probe and receiver channels of the second ultrasound probe, and a second image representing a TOF change between transducer channels of the second ultrasound probe and receiver channels of the first ultrasound probe;

using region of interest (ROI) compression, transforming the first input image pair into a second input image pair representing a TOF change in a virtual ROI by transforming a value measured at an actual distance between the ultrasound probes into a value measured at a fixed distance of the virtual ROI having a same distance as an ROI that has been used for training a neural network;

obtaining a quantitative image reconstructed from the second input image pair, by using the neural network trained to reconstruct a quantitative feature from an input image pair; and restoring the quantitative image for the virtual ROI to a quantitative image for the measured ROI having the actual distance, wherein the ROI compression transforms the value measured at the actual distance into the value measured at the fixed distance of the virtual ROI as follows:

$$U_{\hat{\omega}}(Tx, Rx) = \frac{U_\omega(Tx, Rx)}{M_\omega(Tx, Rx)}$$

where $U_{\hat{\omega}}(Tx, Rx)$ denotes the value measured at the fixed distance of the virtual ROI, $U_\omega(Tx, Rx)$ denotes the value measured at the actual distance, Tx denotes transmission of the ultrasound probes, Rx denotes reception of the ultrasound probes, and $M_\omega(Tx, Rx)$ denotes a compression matrix, $\omega$ denotes the actual distance, and $\hat{\omega}$ denotes the fixed distance of the virtual ROI.

2. The method of claim 1, wherein, by using TOF change images of virtual tissues modeled with speed-of-sound distribution, the neural network is trained to reconstruct the speed-of-sound distribution of the corresponding virtual tissues.

3. The claim of claim 1, wherein, by using signal strength change images of virtual tissues modeled with an attenuation coefficient distribution, the neural network is trained to reconstruct the attenuation coefficient distribution of the corresponding virtual tissues.

4. The method of claim 1, wherein the neural network is trained to reconstruct a speed-of-sound distribution from TOF change images under a guidance of a priori information,
wherein the a priori information is a geometric image of a virtual tissue modeled in an arbitrary shape, and
wherein the TOF change images are images representing TOF change of the ultrasound data having penetrated the virtual tissue modeled with the speed-of-sound distribution.

5. The method of claim 1, wherein the neural network is trained to reconstruct an attenuation coefficient distribution from signal strength change images under a guidance of a priori information,
wherein the a priori information is a geometric image of a virtual tissue modeled in an arbitrary shape, and
wherein the signal strength change images are images representing signal strength change of the ultrasound data having penetrated the virtual tissue modeled with the attenuation coefficient distribution.

6. The method of claim 1, wherein $M_\omega(Tx, Rx)$ is defined as follows:

$$M_\omega(Tx, Rx) \approx \frac{|\vec{r}(Tx, \hat{\omega}) - \vec{r}(Rx, \hat{\omega})|}{|\vec{r}(Tx, \hat{\omega}) - \vec{r}(Rx, \hat{\omega})|}$$

where $\vec{r}$ denotes a position vector.

7. The method of claim 1, wherein the ultrasound-traverse data comprises a first direction traverse data that the second ultrasound probe obtains from an ultrasound signal emitted by the first ultrasound probe of the pair of ultrasound probes, and a second direction traverse data that the first ultrasound probe obtains from an ultrasound signal emitted by the second ultrasound probe of the pair of ultrasound probes.

8. The method of claim 7, wherein the quantitative feature is a speed-of-sound distribution.

9. The method of claim 7, wherein the first input image pair comprises
a first image representing a change in signal strength between transducer channels of the first ultrasound probe and receiver channels of the second ultrasound probe, and
a second image representing a change in signal strength between transducer channels of the second ultrasound probe and receiver channels of the first ultrasound probe, and
wherein the quantitative feature is an attenuation coefficient distribution.

10. The method of claim 1, further comprising:
creating a geometric image of the measurement target, by using ultrasound-echo data reflected from the measurement target among the ultrasound data;
creating the geometric image compressed into the virtual ROI through the ROI compression; and
inputting the compressed geometric image as a priori information of the trained neural network.

11. The method of claim 10, wherein the trained neural network extracts a feature of the second input image pair, and decodes the feature by combining the feature with the compressed geometric image input as the a priori information and outputs the quantitative image for the virtual ROI.

12. The method of claim 10, wherein creating the geometric image of the measurement target comprises creating a B-mode (brightness-mode) image by using the ultrasound-echo data, and creating the geometric image representing a shape of a target from the B-mode image.

* * * * *